(12) United States Patent
Secrest et al.

(10) Patent No.: US 7,691,110 B2
(45) Date of Patent: Apr. 6, 2010

(54) SNARE INJECTION DEVICE

(75) Inventors: Dean J. Secrest, Concord, OH (US); K. Randall John, Chardon, OH (US); Robert M. Stuba, Macedonia, OH (US); Christopher J. Kaye, Concord, OH (US); Jon Eric Younker, Mentor, OH (US)

(73) Assignee: U.S. Endoscopy Group, Inc., Mentor, OH (US)

( * ) Notice: Subject to any disclaimer, the term of this patent is extended or adjusted under 35 U.S.C. 154(b) by 315 days.

(21) Appl. No.: 11/137,814

(22) Filed: May 25, 2005

(65) Prior Publication Data
US 2005/0267490 A1 Dec. 1, 2005

Related U.S. Application Data

(60) Provisional application No. 60/574,073, filed on May 25, 2004.

(51) Int. Cl.
*A61B 17/24* (2006.01)
(52) U.S. Cl. ........... 606/113; 604/164.01; 600/104
(58) Field of Classification Search ......... 606/110–115, 606/46, 127, 128; 604/164.01, 164.04, 164.08, 604/164.09–165.02, 164.05, 44, 171, 272–274, 604/264; 600/104, 106, 153, 101
See application file for complete search history.

(56) References Cited

U.S. PATENT DOCUMENTS

| 4,966,589 | A | * | 10/1990 | Kaufman | .................. 604/174 |
|---|---|---|---|---|---|
| 5,009,642 | A | | 4/1991 | Sahi | |
| 5,156,590 | A | | 10/1992 | Vilmar | |
| 5,190,542 | A | | 3/1993 | Nakao et al. | |
| 5,201,740 | A | | 4/1993 | Nakao et al. | |
| 5,336,227 | A | | 8/1994 | Nakao et al. | |
| 5,374,273 | A | | 12/1994 | Nakao et al. | |
| 5,417,697 | A | | 5/1995 | Wilk et al. | |
| 5,423,830 | A | | 6/1995 | Schneebaum et al. | |
| 5,486,182 | A | * | 1/1996 | Nakao et al. | ................. 606/114 |
| 5,542,948 | A | | 8/1996 | Weaver et al. | |
| 5,666,970 | A | * | 9/1997 | Smith | ......................... 600/585 |
| 5,741,271 | A | | 4/1998 | Nakao et al. | |

(Continued)

FOREIGN PATENT DOCUMENTS

JP 3250621 8/1993

OTHER PUBLICATIONS

Juan-Marie et al., Double-Lumen Snare Injector: Introducing the Double-Lumen Concept in Ancillary Pollypectomy Equipment, Gastrointestinal Endoscopy, vol. 57, No. 5, 2003.

(Continued)

*Primary Examiner*—Anhtuan T Nguyen
*Assistant Examiner*—Kathleen Sonnett
(74) *Attorney, Agent, or Firm*—Calfee, Halter & Griswold LLP

(57) ABSTRACT

A snare injection device for performing endoscopic transection procedures is disclosed. The device includes a snare system and a needle system, each containing actuator components separately routed in one of two channels of an elongated dual lumen. Deployment of the snare and needle are independently operated by two separate handle controls. The device includes needle travel stop and anti-puncture features for safety and ease of use.

15 Claims, 3 Drawing Sheets

U.S. PATENT DOCUMENTS

| | | | |
|---|---|---|---|
| 5,759,187 A | | 6/1998 | Nakao et al. |
| 5,810,776 A | * | 9/1998 | Bacich et al. ............... 604/131 |
| 5,843,051 A | * | 12/1998 | Adams et al. ............... 604/525 |
| 5,846,248 A | * | 12/1998 | Chu et al. ................... 606/114 |
| 5,906,621 A | * | 5/1999 | Secrest et al. ............... 606/114 |
| 5,961,526 A | * | 10/1999 | Chu et al. ................... 606/113 |
| 5,964,740 A | * | 10/1999 | Ouchi ......................... 604/264 |
| 5,997,547 A | * | 12/1999 | Nakao et al. ................ 606/114 |
| 6,007,546 A | * | 12/1999 | Snow et al. ................. 606/113 |
| 6,068,603 A | | 5/2000 | Suzuki |
| 6,093,195 A | * | 7/2000 | Ouchi ......................... 606/113 |
| 6,123,665 A | | 9/2000 | Kawano |
| 6,190,353 B1 | * | 2/2001 | Makower et al. .......... 604/95.01 |
| 6,210,416 B1 | * | 4/2001 | Chu et al. ................... 606/113 |
| 6,352,503 B1 | | 3/2002 | Matsui et al. |
| 6,375,661 B2 | | 4/2002 | Chu et al. |
| 6,458,074 B1 | | 10/2002 | Matsui et al. |
| 6,527,753 B2 | | 3/2003 | Sekine et al. |
| 6,827,710 B1 | * | 12/2004 | Mooney et al. ............. 604/500 |
| 6,945,956 B2 | * | 9/2005 | Waldhauser et al. ...... 604/95.01 |
| 7,001,354 B2 | * | 2/2006 | Suzuki et al. ............... 604/6.11 |
| 7,037,291 B2 | * | 5/2006 | Lee et al. ................ 604/103.04 |
| 2003/0216753 A1 | | 11/2003 | Nishtala et al. |

OTHER PUBLICATIONS

International Search Report from PCT International Application No. PCT/US/05/18294, dated May 25, 2005, 10 pages.

* cited by examiner

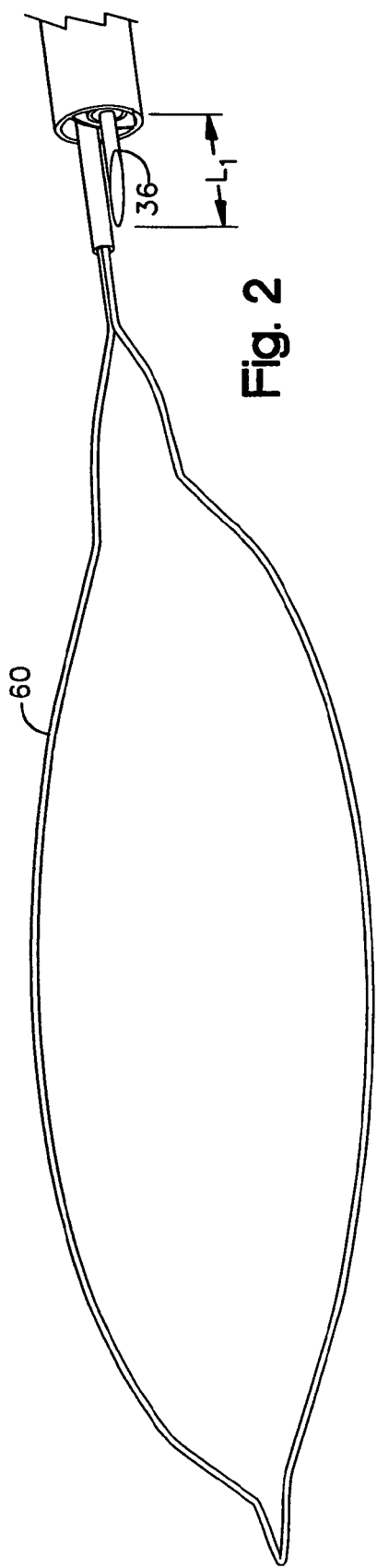

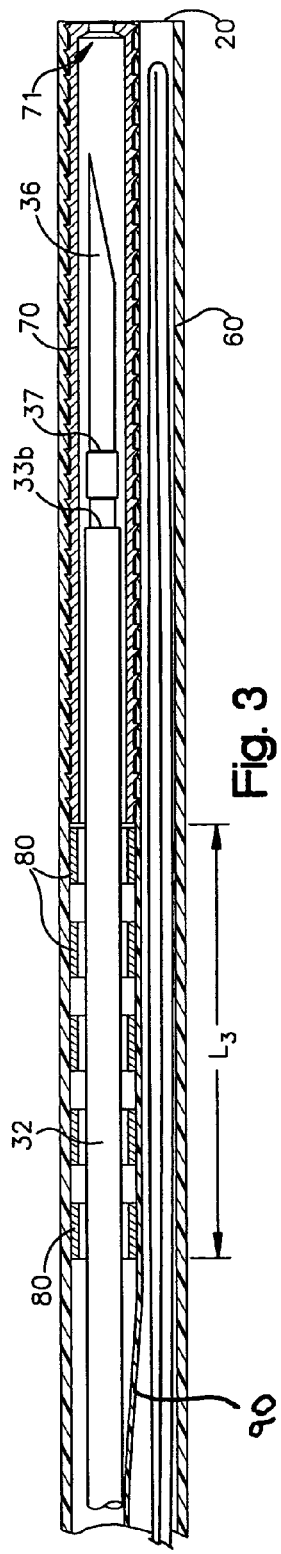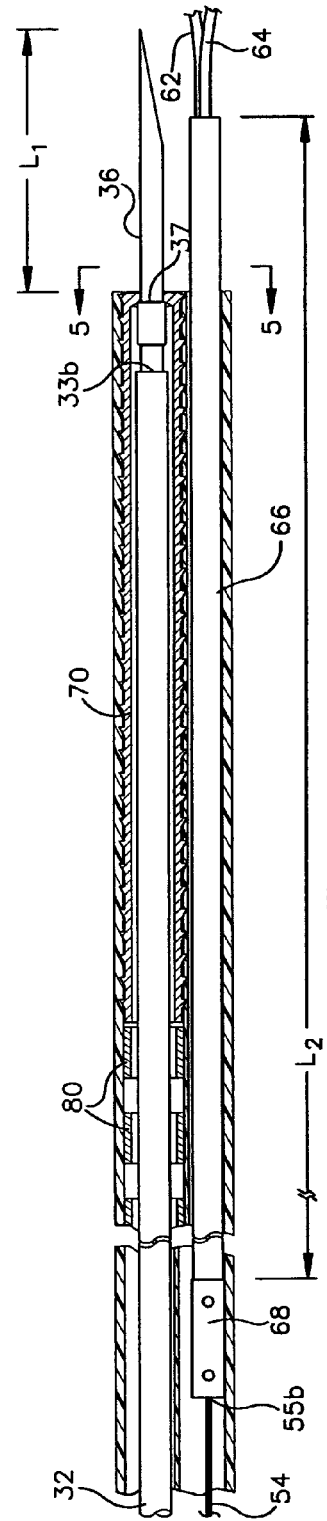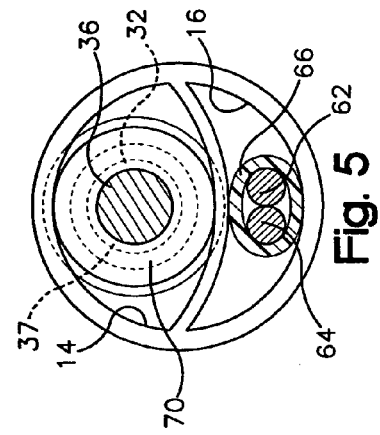

SNARE INJECTION DEVICE

CROSS-REFERENCE TO RELATED APPLICATIONS

This non-provisional application claims the benefit of U.S. Provisional Patent Application No. 60/574,073, entitled "Snare Injection Device," filed May 25, 2004, which is hereby incorporated in its entirety.

FIELD OF THE INVENTION

The present invention relates to an endoscopic medical device and more particularly to a snare injection device for performing endoscopic transection procedures.

BACKGROUND OF THE INVENTION

Endoscopes are well-known in the art and are commonly used for numerous medical procedures. One such procedure is removing polyps, lesions or other types of targeted tissue from the gastrointestinal mucosal wall of a human subject.

Several drawbacks exist with conventional polypectomy removal techniques. Various cauterization devices have been developed to remove polyps. However, these devices sometimes cause serious thermal injury to the gastrointestinal wall, fail to remove the entire targeted tissue, or do not completely cauterize blood vessels which lead to excessive bleeding. Snare devices designed to encircle and remove polyps may not capture all the targeted tissue. Further, a physician may experience difficulty in securing the targeted tissue with the snare. Snaring only the minimal tissue required from the three layer wall, i.e., mucosa, submucosa, and muscularis, is also important. More specifically, to prevent complications, the muscularis tissue should be avoided in this type of procedure. In an effort to solve these and other problems, one technique used is sub-mucosal lift polypectomy which involves injecting the tissue with, for example a saline solution, to lift the tissue to a more favorable position. This technique improves complete transection. The injected fluid separation also insulates the outer muscle from cautery or thermal injury.

Various other procedures require a needle and a snare, including use of a needle to wash the site, applying dies for the purpose of highlighting diseased or abnormal tissue, for injecting tattoo medium for post-transection surveillance purposes, and hemostatic injection therapy for post-polypectomy bleeding. In these and other procedures requiring a snare and a needle, a physician must use two separate auxiliary instruments, and one at a time feed them in and out of the instrument channel, which increases the overall procedure time. Therefore, a need exists in the art for a snare injection device that offers an improvement over prior art designs.

The present invention is a device that includes a snare and a needle, each separately routed in one channel of a dual channel lumen. The needle may perform several functions during the procedure, including pre-procedure and post-procedure injections, and lifting the tissue during the procedure. The present invention also allows for immediate repeat injections which may be required due to absorption of the lift fluid by the gastrointestinal wall, without removal of the snare.

The present invention offers numerous other improvements over prior art needle devices including a needle limit mechanism, consistent 1:1 handle/needle axial movement in a variety of endoscope configurations, and puncture prevention features. In certain prior art designs, a needle could injure a patient by puncturing the sidewall of a device or deploying beyond a desired length to cause harm to a patient. As such, the present invention offers improvements in patient safety and ease of use for the physician.

SUMMARY OF THE INVENTION

In several illustrated embodiments of the present invention, a snare injection device for performing endoscopic polypectomy procedures is disclosed. It should be apparent to others with ordinary skill in the art that use of this device is not limited to polyp removals, but may also be used with other procedures, such as endoscopic mucosal resections (EMR), adherent blood clot removal, or any other purpose requiring transection and/or injections.

In an embodiment of the present invention, a device includes a dual lumen having a first and second channel, a fluid delivery system, and a snare system. The fluid delivery system includes a hollow base, an actuator inserted through the base and the first channel, a hollow knob fixed to the actuator tube proximal end, and a needle fixed to the actuator tube distal end. The snare system includes a body connected to the base, a handle mounted to and movable relative to the body, a cable having a proximal end fixed to the handle that extends substantially through the second channel, and a snare fixed to the cable distal end.

Further features and advantages of the invention will become apparent from the following detailed description made with reference to the accompanying drawings.

The Detailed Description of the Invention merely describes preferred embodiments of the invention and is not intended to limit the scope of the claims in any way. Indeed, the invention as described by the claims is broader than and unlimited by the preferred embodiments, and the terms in the claims have their full ordinary meaning.

BRIEF DESCRIPTION OF THE DRAWINGS

FIG. 2 is an enlarged perspective view of the distal end of the device of FIG. 1, showing the snare and needle deployed;

FIG. 3 is a cross-sectional view of the distal end of the device of FIG. 1, showing the snare and needle in a stored position;

FIG. 4 is a cross-sectional view of the distal end of the device of FIG. 1, showing the snare and needle in a deployed position; and FIG. 5 is an enlarged sectional view of the distal end of the device of FIG. 1, shown along the lines 5-5 in FIG. 4.

DESCRIPTION OF THE INVENTION

Figure 1:
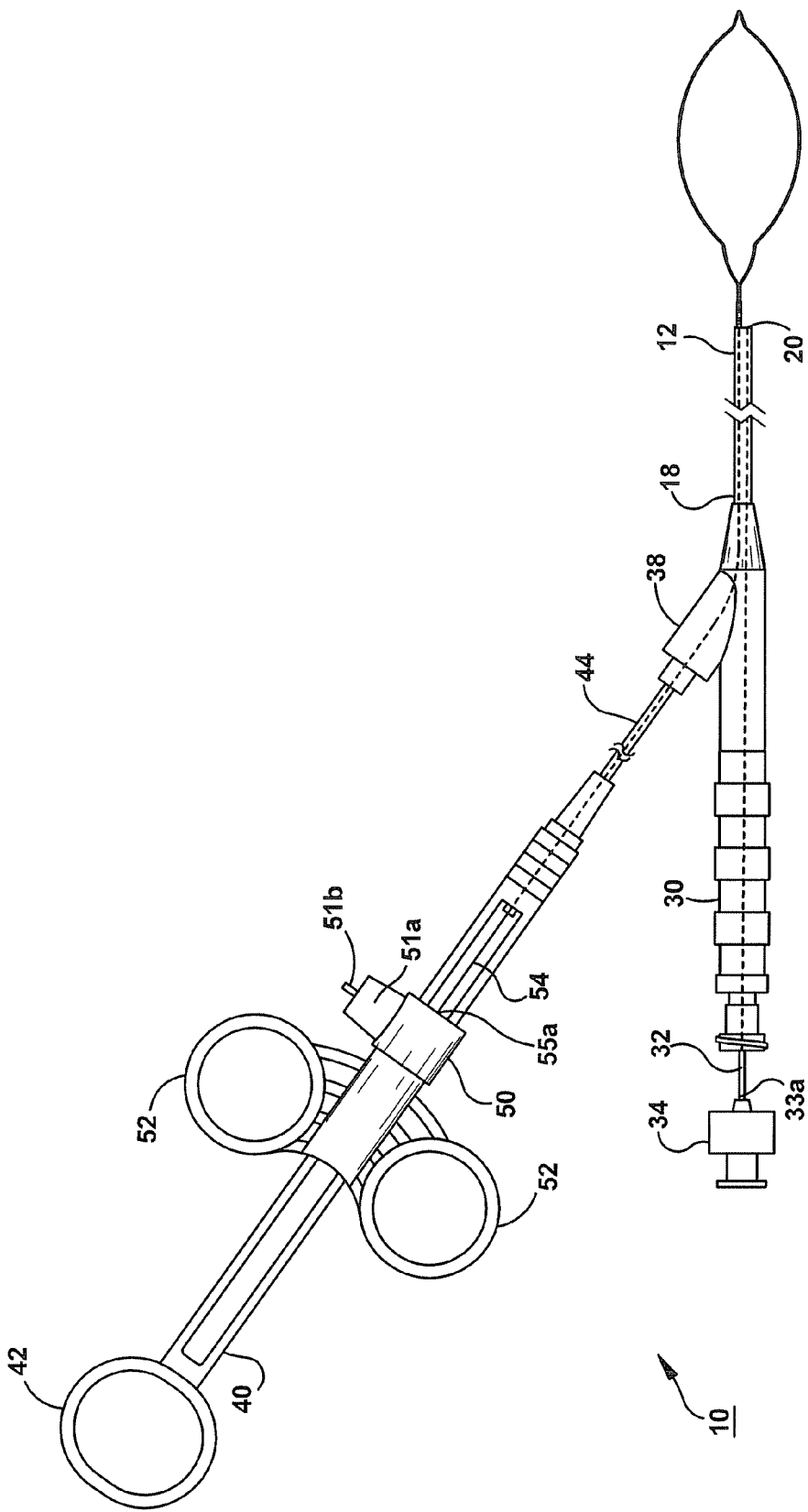
FIG. 1 is a perspective view of a snare injection device constructed in accordance with one embodiment of the present invention, showing the snare deployed.

A snare injection device for performing endoscopic transection procedures is disclosed. The snare and needle are individually routed within a lumen of a dual lumen member. The needle and snare are independently deployable by manipulation of separate control handles by one or two medical operators.

In discussing the device, the terms distal and proximal are used with respect to the operator's hand. In other words, when the device is used within the auxiliary channel of an endoscope or similar device, the proximal and distal orientation are relative to the surgeon or operator of the device.

Referring now to the Figures, a snare injection device 10 for use with an endoscope is illustrated in FIG. 1. The device is suitable for use in polypectomy procedures and any other procedure in which injection and snare capability is required.

In FIG. 1, the snare is shown in an expanded position. FIG. 2 is an enlarged perspective view of the distal end of the device 10, showing the snare 60 expanded and the needle 36 deployed. The device allows a physician to perform either technique without removing the device from the instrument channel.

The device includes an elongated dual lumen 12. The dual lumen has a first channel 14 and a second channel 16, each channel leading from a proximal end 18 to a distal end 20. The lumen 12 shown in a single piece of extruded plastic. The lumen 12 may be constructed from a variety of flexible materials, such as for example, polytetrafluoroethylene (PTFE) or polyethylene tubing. Various first and second channel sizes and shapes may be used in the practice of the present invention. Further, it should be apparent to one with ordinary skill in the art that the present invention may be practiced with a single piece of extruded dual lumen tubing, or alternatively, with a dual lumen assembly including separate tubing and a sheath or other suitable covering.

A fluid delivery system for use to inject tissue within the body is part of the device 10. The delivery system includes a hollow base 30 fixed to a proximal end 18 of the lumen 12. The base 30 provides support for an actuator tube 32 that is threaded through the base and can be moved relative thereto. The tube 32 has a proximal end 33a and a distal end 33b. As shown, the tube 32 is inserted through the base 30 and the first channel 14.

The base 30 further includes a side entry port 38. As shown, this port 38 is angled less than 45 degrees with respect to a longitudinal axis of the base 30. It is believed this angled structure reduces binding within the dual lumen 12. The resulting y-shaped base may be a single molded piece or a two part assembled piece.

The actuator tube 32 can be manipulated by movement of a hollow knob 34. The knob 34 is fixed to said actuator tube 32 proximal end 33a. A needle 36 is illustrated fixed to the actuator tube 32 distal end 33b. In this position, a fluid solution can be passed under pressure through the knob to the needle.

Referring now to FIGS. 3 and 4, a range of motion of the needle 36 is illustrated. FIG. 3 is a cross-sectional view of the distal end of the 10 device, showing the needle 36 in a stored position. In this at rest position, no axial forces are on the needle 36. The needle is disposed within a needle housing member 70. The housing shown is an elongated barb fitting 70 with a hollow interior and a threaded, notched, or intermittedly tapered exterior surface, or otherwise generally relieved body, which offers improved flexibility. Other fittings may be used that are known in the art. Consequently, the needle cannot puncture the sidewalls of the lumen 12 in a stored position.

Adjacent to distal end 20 of the dual lumen, the barb 70 may be disposed in place by being heat shrunk, press fit, bonded, or other suitable known method. The barb may be constructed from any coated metal or non-conductive suitable material, such as for example, a medium hardness plastic. It is important that the barb be non-conductive so that radio frequency energy used to energize the snare does not transfer to the barb which in turn would direct the current away from the targeted tissue. The barb may include two or more pieces joined together.

After visual identification of targeted tissue, a physician protrudes the needle into the tissue and injects a fluid. A needle 36 in a protruded position is shown in FIG. 4. The actuation step to protrude the needle 36 is manipulation of the knob 34 in a direction of the needle 36. The knob 34, actuator tube 32 and needle 36 all move axially in a 1:1 distance relationship. The distance $L_1$ the needle protrudes is predetermined by a needle stop 37 interfering with a narrowed portion 71 of the barb 70. The distance $L_1$ is determined by performance and safety criteria, and can vary in the practice of the present invention.

FIG. 4 shows the needle stop 37 shoulder contiguous with the narrow portion 71 in a fully protruded position. The stop 37 and narrowed portion 71 prevent the needle from falling off into the patient if the needle would ever disconnect with the actuator tube 32.

The relationship of the tube 32 and the base 30 is configured to have additional stroke length to overcome any articulate friction or loss motion in the elongated lumen 12 so that full needle projection will occur. After the knob 34 is released, a spring mechanism (not shown) disposed internally in the base 30 forces the knob 34 and needle 36 to return to their at rest position as shown in FIG. 1.

A snare system for transecting tissue is included in the device 10. The snare system can be used to remove tissue, such as for example, a polyp after it has been lifted by the injection of a fluid. The snare 60 is shown in a collapsed position in FIG. 3.

The system includes an elongated body 40 having a thumb ring 42 at a proximal end. A handle 50 is formed on the body 40 as a separate piece. The handle is slidable relative to the body in either a distal or proximal direction by manipulation of two finger rings 52. The base 40 and handle 50 are formed of a rigid plastic material, although any suitable material may be used in the practice of the present invention.

The snare system 10 includes a cable 54 that extends substantially through the second channel 16 of the dual lumen 12. The cable 54 has a proximal end 55a fixed to the handle 42 and a distal end 55b fixed to a connector 68. As shown, the cable 50 further passes through a flexible tube 44 the remotely connects the body 40 to the inlet port 38. The tube 44 can be constructed from any flexible durable material such as polyethylene.

FIGS. 2 and 4 show the snare 60 in an expanded position. The snare 60 is fixed to the distal end of the cable 54 by a connector 68. The snare 60 is formed by a wire loop having two ends 62 and 64, as best seen in FIGS. 4 and 5. An enlarged sectional view of the distal end of the device 10 is shown in FIG. 5. To prevent the wires from crossing and kinking which causes excessive friction and binding of the cable mechanism, a length $L_2$ of the wires is bound by heat shrink material 66. This feature also allows for the connector 68 to be positioned more proximately inside the second channel 16 so it will not exit the tube 12 distal end 20. This proximal position prevents any chance of the connector 68 exiting the tube 12 and catching upon the distal end 20 upon reentry inside the second channel 16.

A series of lumen expanding spacers 80 are illustrated in FIGS. 3 and 4 in the first channel 14. The spaces may be press fit, glued, heat inserted or any other suitable method. A total of five equally spaced and sized spacers are shown for exemplary purposes only, although the number, size and spacing of the spacers 80 may vary in the practice of the present invention. The most distal spacer is position axially at the end of the barb 70. To provide enough space for the needle mechanism to function, the barb 70 occupies over half of the diameter of the distal end portion. As a result, the barb causes sagging of the center membrane that separates the first 14 and second channel 16 at the distal portion of the tube. The spacers 80 effectively provide an extension of the sagging of the first channel 14 for a length $L_3$ as shown.

The extension of the sagging portion provides additional length for travel of the snare loop. In particular, the section of the unsupported wires 62, 64, i.e., the section uncovered by heat shrink 66, can shift up or down within the second channel 16. The shifting of the wires does not readily transition through the shifting transition area 90 of the center membrane. So therefore, the spacers 80 provide additional length of the reduced lumen so the unsupported wires 62, 64 does not reach the transition area.

It should be understood by others with ordinary skill in the art that the length $L_3$ can vary in the practice of the present invention, as can the positioning of the spacers relative to the heat shrink 66, the connector 68, the tube distal end 20, or other components of the device 10.

While several embodiments of the invention has been illustrated and described, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the annexed claims.

What is claimed is:

1. A snare injection device for performing an endoscopic procedure to remove targeted tissue, the device comprising:
    a) an elongated member having a first channel and a second channel separated by a plastic membrane;
    b) a needle system for inserting a needle into said target tissue, said needle system comprising a needle, a hollow actuator tube, and a tube handle, wherein said tube is inserted through said first channel;
    c) a snare system for transecting said targeted tissue, said snare system comprising a snare apparatus, an actuating cable, and a snare handle, wherein said cable is inserted through said second channel;
    d) a base, wherein said tube and said cable are routed therethrough; and
    e) a flexible needle housing positioned between said needle and said elongated member when said needle is in a relaxed position;
    f) wherein said needle housing has a continuous inner surface and prevents said needle from penetrating said plastic membrane;
    g) further wherein said needle housing is disposed within a distal end of said first channel such that a cross-sectional area of said first channel is non-collapsible and greater than a cross-sectional area of said second channel along an entire length of said needle housing, and a cross-sectional area of said first channel is collapsible along at least a length of said elongated member proximal said needle housing.

2. The snare injection device of claim 1 wherein said base is a y-shaped molded uniform piece.

3. The snare injection device of claim 1 wherein said base comprises an elongated hollow member having an inlet and an outlet and a port between said inlet and outlet disposed at an angle between 0 degrees and 90 degrees to a longitudinal axis of said first member.

4. The snare injection device of claim 1 wherein said needle housing is disposed within a distal end of said first channel such that a distal end of said second channel comprises a first and a second non-linear circumferential edge defining a crescent shaped cross section along the length of said needle housing.

5. The snare injection device of claim 1 wherein said elongated member is a single extruded piece of dual lumen plastic.

6. The snare injection device of claim 1 wherein said needle housing comprises at least one barb fitting.

7. The snare injection device of claim 1 further comprising a distal needle stop.

8. The snare injection device of claim 1 wherein said needle housing is a flexible elongated barb that is positioned between said needle and said first channel of said elongated member when said needle is in said relaxed position.

9. The snare injection device of claim 1 further comprising at least one lumen expanding spacer disposed with said first channel.

10. The device of claim 1 further wherein said needle housing is an elongated barb positioned between said needle and said first channel having a distal portion with an inner diameter, wherein said device comprises a needle stop with an outer diameter greater than said inner diameter.

11. The snare injection device of claim 1 wherein said needle housing is non-conductive such that energy used to energize said snare apparatus does not transfer to said needle housing and direct current away from said targeted tissue.

12. A snare injection device for performing an endoscopic procedure to remove targeted tissue, the device comprising:
    a) an elongated member having a first channel and a second channel;
    b) a needle system for inserting a needle into said target tissue, said needle system comprising a needle, a hollow actuator tube, and a tube handle, wherein said tube is inserted through said first channel;
    c) a snare system for transecting said targeted tissue, said snare system comprising a snare apparatus, an actuating cable, and a snare handle, wherein said cable is inserted through said second channel;
    d) a base, wherein said tube and said cable are routed therethrough;
    e) a flexible needle housing positioned between said needle and said first channel of said elongated member when said needle is in a relaxed position; and
    f) a spring disposed in said base that limits movement of said needle in a direction of said needle housing;
    g) wherein said needle housing prevents said needle from penetrating said first channel;
    h) wherein said needle housing has a continuous inner surface and is disposed within a distal end of said first channel such that a cross-sectional area of said second channel is non-collapsible and less than a cross-sectional area of said first channel along a length of said needle housing and a cross-sectional area of said first channel is collapsible relative a cross-sectional area of said second channel along at least a length of said elongated member proximal said needle housing.

13. A snare injection device for performing an endoscopic procedure to remove targeted tissue, the device comprising:
    a) an elongated member having a first channel and a second channel separated by a plastic membrane;
    b) a needle system for inserting a needle into said target tissue, said needle system comprising a needle, a hollow actuator tube, and a tube handle, wherein said tube is inserted though said first channel;
    c) a snare system for transecting said targeted tissue, said snare system comprising a snare apparatus, an actuating cable, and a snare handle, wherein said cable is inserted though said second channel;
    d) a base, wherein said tube and said cable are routed therethrough; and
    e) a flexible needle housing positioned between said needle and said elongated member when said needle is in a relaxed position;

f) wherein said needle housing acts as a spacer to maintain a constant ratio between a cross-sectional area of said first channel and a cross-sectional area of said second channel along a length of said needle housing, such that a cross-sectional area of said first channel is non-collapsible and greater than a cross-sectional area of said second channel along an entire length of said needle housing, and a cross-sectional area of said first channel is collapsible along a length of said plastic membrane proximal said needle housing.

14. A snare injection device for performing an endoscopic procedure to remove targeted tissue, the device comprising:

an elongated member adapted for insertion into an endoscope instrument channel and having a first channel and a second channel separated by a plastic membrane;

a needle system for inserting a needle into said target tissue, said needle system comprising a needle, a hollow actuator tube, and a tube handle, wherein said tube is inserted through said first channel;

a snare system for transecting said targeted tissue, said snare system comprising a snare apparatus, an actuating cable, and a snare handle, wherein said cable is inserted though said second channel;

a base, wherein said tube and said cable are routed therethrough; and a flexible needle housing positioned at a distal end of said first channel;

wherein said needle housing has a continuous inner surface and prevents said needle from penetrating said plastic membrane;

further wherein said needle housing is disposed within a distal end of said first channel such that a cross-sectional area of said first channel is non-collapsible and greater than a cross-sectional area of said second channel along an entire length of said needle housing, and a cross-sectional area of said first channel is collapsible along at least a length of said elongated member proximal said needle housing.

15. The snare injection device of claim 14 wherein a position of said membrane is fixed along the length of said needle housing, and unfixed along at least a length of said elongated member proximal said needle housing.

* * * * *